United States Patent [19]

Salamon

[11] 4,171,312

[45] Oct. 16, 1979

[54] ALKYL 7-[TETRAHYDRO-4-(3-HYDROXY-1-OCTENYL)-2,6-DIOXO-4H-CYCLOPENTA-1,3-DIOXOL-5-YL]-5-HEPTENOATES

[75] Inventor: Karlene W. Salamon, Chicago, Ill.

[73] Assignee: G. D. Searle & Co., Skokie, Ill.

[21] Appl. No.: 903,470

[22] Filed: May 8, 1978

[51] Int. Cl.² ........................................... C07D 317/44
[52] U.S. Cl. .................................. 260/340.2; 424/285
[58] Field of Search ...................................... 260/340.2

[56] References Cited

PUBLICATIONS

G. Doria et al., Il Farmaco, Ed. Sc., vol. 29(4), (1974), pp. 327–330.

*Primary Examiner*—Norma S. Milestone
*Attorney, Agent, or Firm*—John M. Brown

[57] ABSTRACT

Preparation of alkyl 7-[tetrahydro-4-(3-hydroxy-1-octenyl)-2,6-dioxo-4H-cyclopenta-1,3-dioxol-5-yl]-5-heptenoates adapted to counteract conception and suppress the activity of 3-methylglutaryl coenzyme A reductase is disclosed.

2 Claims, No Drawings

ALKYL 7-[TETRAHYDRO-4-(3-HYDROXY-1-OCTENYL)-2,6-DIOXO-4H-CYCLOPENTA-1,3-DIOXOL-5-YL]-5-HEPTENOATES

This invention relates to alkyl 7-[tetrahydro-4-(3-hydroxy-1-octenyl)-2,6-dioxo-4H-cyclopenta-1,3-dioxol-5-yl]-5-heptenoates and a process for the preparation thereof. More particularly, this invention provides new, useful, and unobvious chemical compounds of the formula

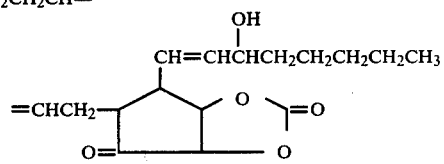

wherein R represents alkyl.

Among the alkyls represented by R, primary alkyls of the formula

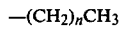

and secondary alkyls of the formula

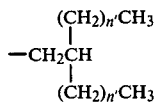

in which the numerical value of n, n', and n" is such that the total carbon content of the enformulated groupings is less than 8 are preferred. Typical of such groupings and especially preferred are methyl, ethyl, propyl, 2-methylpropyl, and butyl.

The compounds to which this invention relates are useful because of their valuable pharmacological properties. Thus, for example, they counteract conception and suppress the activity of 3-hydroxy-3-methylglutaryl conenzyme A (HMG Co A) reductase, an enzyme which controls the rate at which cholesterol is synthesized in mammalian liver, one of the two principal sources of serum cholesterol.

The contraceptive utility of the instant compounds is evident from the results of a standardized test for their capacity to inhibit the fecundity of hamsters. In this test, sexually-mature female Syrian golden hamsters weighing at least 105 g are mated; and to each of a group of 5 is administered, daily for 5 days beginning on the first day sperm appears in the vagina between 8:15 and 10:00 a.m., test compound dissolved or suspended in an inert vehicle. The initial daily dose is ordinarily 50 mg/kg in 0.2 ml of corn oil, subcutaneously or intragastrically. A group of such animals to which is likewise administered vehicle alone serves as controls. Approximately 48 hr. after the 5th dose, the animals are sacrificed and their uteri and ovaries inspected for implantation sites and corpora lutea. If the total number of the former divided by the total number of the later (i.e., the implantation rate) affords a value amounting to 0.5 or less, the compound is considered to inhibit fecundity in the foregoing test. The $ED_{50}$ of such a compound is determined by repeating the test at appropriate doosage(s). Potency is expressed as the ratio of the $ED_{50}$ of estrone to that of compound. Methyl 7-[tetrahydro-4-(3S-hydroxy-1E-octenyl-2,6-dioxo-4H-cyclopenta-1,3-dioxol-5-yl]-5Z-neptenoate, the product of Example 1 hereinafter, inhibited fecundity via the foregoing procedure at a dosage of 10 mg/kg administered subcutaneously in corn oil, at which dose the implantation rate was 0.16. The $ED_{50}$ of the compound was found to be 5.6 mg/kg and its potency approximately 1% that of estrone.

Those skilled in the art will rrecognize that observations of activity in standardized tests for particular pharmacological effects are fundamental to the development of valuable new drugs, both veterinary and human.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved or suspended in water or a comparably innocuous liquid. Parenteral administration may be effected via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et al., "Remington's Pharmaceutical Sciences", 14 Ed., Merck Publishing Company, Eaton, Pa., 1965.

Appropriate dosages, in any given instance, of course depend upon the nature and severity of the condition treated, the route of administration, and the species of mammal involved, including its size and any individual idiosyncrasies which obtain.

Preparation of compounds of this invention proceeds by contacting a 7-[3,4-epoxy-5-(3-hydroxyl-1-octenyl)-2-oxocyclopentyl]-5-heptenoic acid with an iodoalkane in a solvent such as N,N-dimethylformamide. Other preparative procedures will be obvious to those skilled in the art of organic chemistry.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials are in parts by weight, except as otherwise noted.

EXAMPLE 1

To a solution of 13 parts of (5Z,13E,15S)-10ξ,11ξ-epoxy-15-hydroxy-9-oxoprosta-5,13-dien-1-oic acid in approximately 250 parts of N,N-dimethylformamide is added 13 parts of sodium bicarbonate. The resultant suspension is stirred at room temperature for 15 minutes, whereupon 32 parts of iodomethane is introduced and stirring then resumed for a further 20 hours. The reaction mixture is thereupon filtered, and the filtrate is extracted with benzene. The extract is washed with water, dried over anhydrous sodium sulfate, and stripped of solvent by vacuum distillation. The residual red oil is dissolved in benzene; and the benzene solution is chromatographed on silica gel, using benzene and mixtures thereof with increasing amounts of ethyl acetate as developing solvents. From an eluate comprising 30% of ethyl acetate in benzene, on evaporation of solvent, methyl 7-[tetrahydro-4-(3S-hydroxy-1E-octenyl)-2,6-dioxo-4H-cyclopenta-1,3-dioxol-5-yl]-5Z-heptenoate is obtained as a pale yellow oil. The product has the formula CH₃OOCCH₂CH₂CH₂CH= 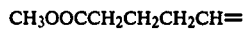
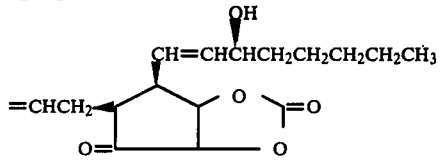

EXAMPLE 2

Substitution of 41 parts of 1-iodo-3-methylpropane for the iodomethane called for in Example 1 affords, by the procedure there detailed, 2-methylpropyl 7-[tetrahydro-4-(3S-hydroxy-1E-octenyl)-2,6-dioxo-4H-cyclopenta-1,3-dioxol-5-yl]-5Z-heptenoate.

EXAMPLE 3

Substitution of 51 parts of 1-iodoheptane for the iodomethane called for in Example 1 affords, by the procedure there detailed, heptyl 7-[tetrahydro-4-(3S-hydroxy-1E-octenyl)-2,6-dioxo-4H-cyclopenta-1,3-dioxol-5-yl]-5Z-heptenoate.

What is claimed is:
1. A compound of the formula

ROOCCH₂CH₂CH₂CH= 
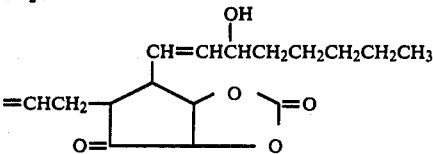

wherein R represents primary alkyl of the formula

—(CH₂)$_n$CH₃ 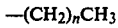

or secondary alkyl of the formula

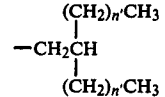

in which the numerical value of n, n' and n" is such that the total carbon content of each grouping represented by R is less than 8.

2. A compound according to claim 1 which is methyl 7-[tetrahydro-4-(3S-hydroxy-1E-octenyl)-2,6-dioxo-4H-cyclopenta-1,3-dioxol-5-yl]-5Z-heptenoate.

* * * * *